US006664423B2

(12) United States Patent
Herwig et al.

(10) Patent No.: US 6,664,423 B2
(45) Date of Patent: Dec. 16, 2003

(54) TWO-PHASE AMMOXIMATION

(75) Inventors: Juergen Herwig, Huenxe (DE); Stefan Leininger, Hanau (DE); Georg Oenbrink, Duelmen (DE); Thomas Schiffer, Haltern (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/293,471

(22) Filed: Nov. 14, 2002

(65) Prior Publication Data

US 2003/0100795 A1 May 29, 2003

(30) Foreign Application Priority Data

Nov. 28, 2001 (DE) .......................................... 101 58 352

(51) Int. Cl.[7] ...................... C07C 249/06; C07C 249/08
(52) U.S. Cl. .................... 564/253; 564/265; 564/269
(58) Field of Search ................................ 564/265, 269, 564/253

(56) References Cited

U.S. PATENT DOCUMENTS

| 4,794,198 A | 12/1988 | Roffia et al. ................. 564/267 |
| 5,312,987 A | 5/1994 | Mantegazza et al. ....... 564/267 |
| 5,498,793 A | 3/1996 | Mantegazza et al. ....... 564/265 |

FOREIGN PATENT DOCUMENTS

| DE | 195 21 011 | 12/1995 |
| EP | 0 267 362 | 5/1988 |
| EP | 0 496 385 | 7/1992 |
| EP | 0 564 040 | 10/1993 |
| EP | 1 227 080 | 7/2002 |

*Primary Examiner*—Peter O'Sullivan

(57) ABSTRACT

Oximes are prepared from ketones or aldehydes, hydrogen peroxide and ammonia. The reaction is carried out in a system of one aqueous phase and one phase of hydrocarbons inert under the reaction conditions in the presence of at least one interphase contactor and a catalyst system which consists of at least two components. A first component of the catalyst system is present in heterogeneous form and is based on titanium, silicon and oxygen and a second component is a homogeneously dissolved or suspended ammonium salt.

20 Claims, No Drawings

TWO-PHASE AMMOXIMATION

BACKGROUND OF THE INVENTION

1. Field of the Invention

The invention relates to a process for preparing an oxime from a ketone or an aldehyde.

2. Discussion of the Background

European patent application EP-A-0 267 362 mentions, in examples 8 and 9, the two-phase preparation of cyclohexanone oxime. Toluene is used as solvent, but has the disadvantage that it is not inert toward concentrated sulfuric acid. This is of critical importance, since, in the case of high-boiling oximes, for example cyclododecanone oxime, the oxime present after the reaction is extracted from a solvent with sulfuric acid. When toluene is used as ammoximation solvent, solvent exchange must first take place, since toluene is not inert toward sulfuric acid. This means an additional process step. In addition, in EP-A-0 267 362, a yield of only <90% is achieved in the two-phase system in example 8. High reaction rates, however, are very important for industrial use in the case of larger rings, for example cyclododecanone, since with increasing molecular weight, the unreacted ketone may only be separated off from the corresponding oxime with great technical complexity. In EP-A-0 267 362, example 9, the ternary solvent mixture toluene, tert-butanol and water is used to prepare cyclohexanone oxime. This ternary solvent mixture has the disadvantage that the oxime present after the reaction is distributed among the two phases and thus complete removal of the oxime by phase separation is not possible. Furthermore, the conversion rates achieved in EP-A 0 267 362, examples 8 and 9, at 1.1 g of oximeg of catalyst-h are low. No example is disclosed of two-phase ammoximation of cyclododecanone.

Eni-Chem, in German laid-open application DE 195 21 011 A1 (equivalent to U.S. Pat. No. 5 498 793) claims a process for ammoximating acetophenone and cyclododecanone. The publication also claims the use of $C_5$–$C_8$ aliphatic hydrocarbons as solvent, without disclosing an example of such a reaction.

SUMMARY OF THE INVENTION

It is therefore an object of the present invention to provide a process for the ammoximation of ketones and aldehydes. In particular, relatively large and bulky ketones such as acetophenone and cyclododecanone should be used as starting materials. The product should be removed completely via phase separation. The conversion at a peroxide yield of >50% should be as complete as possible. The conversion rate should be in an industrially acceptable range and the solvent used should be inert toward sulfuric acid. The conversion should be, if possible, so high that subsequent reaction with an aqueous hydroxylamine solution, as described by Eni-Chem in European patent application EP-A-0 564 040 for the example of cyclohexanone can be omitted.

This and other objects have been achieved by the present invention the first embodiment which includes a process for preparing an oxime, comprising:

reacting a ketone or an aldehyde with hydrogen peroxide and ammonia in a system of one aqueous phase and one phase consisting of a hydrocarbon inert under the reaction conditions, in the presence of a catalyst system which comprises at least two components; and wherein a first component of the catalyst system is present in heterogeneous form and is based on titanium, silicon and oxygen; and wherein a second component is a homogeneously dissolved or suspended ammonium salt; and wherein at least one interphase contactor is present.

DETAILED DESCRIPTION OF THE INVENTION

Surprisingly, it has now been found that ketones and aldehydes can be ammoximated in the presence of hydrocarbons inert under the reaction conditions. A high conversion rate and peroxide yield is achieved in the presence of a titanium silicalite as heterogeneous catalyst if ammonium salts are added as homogeneous or suspended cocatalyst and one or more interphase contactors are added.

The present invention therefore relates to a process for preparing oximes by reacting ketones or aldehydes with hydrogen peroxide and ammonia in a system of two liquid phases. One phase is an aqueous system and the other phase contains at least one hydrocarbon inert under the reaction conditions. The reaction proceeds in the presence of a catalyst system which consists of at least two components. One component is based on titanium, silicon and oxygen, preferably in the form of a titanium silicalite. The second component is an ammonium salt which is preferably in homogeneous dissolved form or, at high concentrations, is also in part suspended. One or more surfactants or a mixture of one or more surfactants and one or more phase-transfer catalysts are also present as interphase contactors. For practical reasons, the number of interphase contactor components is in each case at most 3, preferably 1.

The catalyst is based on titanium, silicon and oxygen. The catalyst is preferably a titanium silicalite which is commercially available, for example, as titanium silicalite TS1.

The catalyst can be used as solid, not only crystalline as powder, but also as shaped body. If the catalyst is used as shaped body, at least one further component consisting of an acidic solid which contains an inorganic or organic support material can also be present in addition to the titanium/silicon/oxygen component. Either the support material itself has Lewis acid or Brönsted acid properties, or corresponding Lewis acid or Brönsted acid functional groups are applied to the support material and such groups are introduced physically or chemically. The support material can at the same time also act as binder of the shaped body. A preferred support material is, for example, an acidic inorganic solid based on aluminum oxide or aluminosilicate. However, the support material can alternatively be an organic solid based on acid or strongly acid ion exchangers.

The weight ratio of catalyst to support material, if used, is preferably from 0.1:1 to 10:1. The weight ratio of catalyst to support material includes all values and subvalues therebetween, especially including 0.5:1, 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1 and 9.5:1.

The catalyst is used in amounts of 0.2–5% by weight, based on the weight of total reaction solution. The amount of catalyst includes all values and subvalues therebetween, especially including 0.5, 1, 1.5, 2. 2.5, 3, 3.5, 4 and 4.5% by weight.

The catalyst can also be disposed in the form of a fixed bed (fixed-bed catalyst) through which the reaction mixture is passed. The residence time in the fixed bed is preferably from 0.1 to 120 seconds, particularly preferably from 0.5 to 60 seconds. The residence time includes all values and subvalues therebetween, especially including 1, 5, 10, 20, 30, 40, 50, 60, 70, 80, 90, 100 and 110 seconds.

As homogeneous cocatalyst for the inventive process, all ammonium salts can be used which are sufficiently soluble in the reaction mixture and whose anions do not have a disadvantageous effect on the course of the reaction. Non-limiting examples are ammonium salts of strong mineral acids, for example ammonium chloride, ammonium sulfate or ammonium nitrate, and ammonium salts of carboxylic acids, for example ammonium formate, acetate, propionate, oxalate, glutarate, citrate or benzoate. The amount of ammonium salt can be chosen within broad limits. Preferably, the ammonium salt is used at a concentration of from 0.001 moukg to 1 mol/kg. The amount of ammonium salt includes all values and subvalues therebetween, especially including 0.005, 0.01, 0.05, 0.1 and 0.5 mol/kg. The ammonium salt is preferably added either directly to the reaction mixture or to the hydrogen peroxide used in the reaction.

In a preferred embodiment of the present invention, the ammonium salt is generated in the reaction mixture from a Brönsted acid and the ammonia used for the reaction. Non-limiting examples of preferred Brönsted acids are mineral acids, for example hydrochloric acid, sulfuric acid and nitric acid, and carboxylic acids, for example formic acid, acetic acid, propionic acid, oxalic acid, glutaric acid, citric acid or benzoic acid. The Brönsted acid is preferably either added directly to the reaction mixture or to the hydrogen peroxide used for the reaction. The cocatalyst remains in the aqueous phase after the reaction.

Interphase contactors used are surfactants, if appropriate in combination with phase-transfer catalysts, provided that they are stable, that is to say they are not oxidized in situ. Preferred examples of surfactants which may be mentioned are alkane sulfonate, in particular the sodium salt of alkanesulfonic acid having 13 to 17 carbon atoms in the unbranched or branched, preferably unbranched, carbon chain (for example Marlon PS 30 from Sasol GmbH) or the sodium salt of alkylbenzenesulfonic acid having 10 to 13 carbon atoms in the unbranched or branched carbon chain (for example Marlon A 315 from Sasol GmbH), without limiting the invention to these surfactants. Mixtures of surfactants can also be used.

Other possible interphase contactors which, if appropriate, can additionally be added to the surfactant are quaternary ammonium salts of the type $NR_1R_2^+R_3R_4^+X^-$, wherein the radicals $R_1–R_4$, independently of one other, can preferably be aliphatic hydrocarbons of $C_1–C_{20}$ and $X^-$ is an anion, for example chloride, bromide, iodide or hydrogen sulfate. Preferred examples are tetrabutylammonium and benzyltriethylammonium salts. Other possible additional interphase contactors are phosphonium salts, for example tetrabutylphosplioniurn salts, onium compounds, crown ethers (especially 18-crown-6) and polyethylene glycols. The interphase contactors are added at concentrations of from 0.01% by weight to 5% by weight, based on the weight of the total reaction mixture. The concentration of the interphase contactor includes all values and subvalues therebetween, especially including 0.05, 0.1, 0.5, 1, 1.5, 2, 2.5, 3, 3.5, 4 and 4.5% by weight.

The reaction proceeds highly selectively with respect to the ammoximation of the carbonyl compound. Even at high conversion rates (>99%), the selectivity of the oxime is greater than 99%, according to GC analysis. If, for example, technical grade cyclododecanone is used, only traces of cyclododecane and cyclododecanol are detected in the GC as by-products, which were already present in the cyclododecanone as impurities. A further by-product detected in a few cases is laurolactam at concentrations of <0.1% and the ketimine cyclododecanonimine, which is formed in the reversible reaction with ammonia, at concentrations of <0.5%.

Solvents forming the second phase are preferably hydrocarbons which are stable toward hydrogen peroxide and ammonia and concentrated sulfuric acid and have sufficient solubility not only for the carbonyl compound but also for the corresponding oxime. Preferably, suitable solvents are $C_6–C_{12}$ aliphatic and cycloaliphatic hydrocarbons. Particularly suitable for the reaction of, for example, cyclododecanone, are isopropylcyclohexane, cyclooctane and cyclododecane, without limiting the invention to these.

Hydrogen peroxide is used as aqueous solution at conventional concentrations, preferably at least 30% strength by weight. Ammonia is fed to the reactor either as concentrated aqueous solution (>20% strength) or preferably as gas. Advantages result in the gaseous addition of ammonia and, in the case of highly concentrated peroxide solutions, from the smaller amount of water which needs to be removed from the homogeneous catalyst during the work up of the reaction mixture.

The reaction temperature of the ammoximation is between 20° C. and 150° C., preferably between 50° C. and 120° C., and particularly preferably between 60° C. and 100° C. The reaction temperature includes all values and subvalues therebetween, especially including 30, 40, 50, 60, 70, 80, 90, 100, 110, 120, 130 and 140° C. The reactor is operated either at atmospheric pressure, that is to say the vapor pressure of the respective solvent at the reaction temperature, or at a slight superatmospheric pressure, preferably between 1 bar and 10 bar. The superatmospheric pressure includes all values and subvalues therebetween, especially including 2, 3, 4, 5, 6, 7, 8 and 9 bar. The superatmospheric pressure can be set using ammonia or an inert gas. If the reactor is closed, the pressure increases due to formation of gaseous decomposition products in side reactions (especially nitrogen and oxygen) during the reaction. It is advantageous to run the reactor isobarically, while gaseous decomposition products are able to escape in a controlled manner via a gentle off-gas stream equipped with a bubble counter, and if appropriate consumed ammonia is replenished.

During the ammoximation reaction, carbonyl compound and hydrogen peroxide can each be added batchwise or continuously. Since decomposition reactions of $H_2O_2$ always occur from time to time, complete conversion of, for example, cyclododecanone, requires an excess of peroxide solution which can be minimized by suitable reaction procedure and the inventive catalyst systems. In the experiments of the present invention, it has proved to be advantageous either to introduce the carbonyl compound at the start of the reaction or to add it in equimolar amounts in parallel to the hydrogen peroxide and to replenish the required excess of peroxide according to consumption after carbonyl addition has been completed.

Ketones and aldehydes used are preferably large and bulky carbonyl compounds having from 8 to 20 carbon atoms. Preferred examples are acetophenone and the cyclic ketones: cyclooctanone, cyclodecanone, cyclododecanone and cyclopentadecanone. However, in principle, all ketones are suitable which are predominantly dissolved in the organic phase in the two-phase amunoximation.

"Conversion" within the meaning of the present invention refers to "reaction" and "conversion rate" refers to "reaction rate."

Having generally described this invention, a further understanding can be obtained by reference to certain specific examples which are provided herein for purposes of illustration only, and are not intended to be limiting unless otherwise specified.

EXAMPLES

In order to ensure exactly identical reaction conditions, in all of the examples in each case fresh catalyst (titanium silicalite TS1, Degussa AG) from the same batch was used. There was no additional catalyst activation before the reaction. The catalyst was removed via a pressure filter after the reaction at 75° C. and thus recovered.

Example 1

In a nitrogen-purged, heatable 1.6l glass pressure reactor (Büchi) equipped with magnetic coupling, gas inlet stirrer (500 rpm), purge and pressure regulator, 91.2 g (500 mmol) of cyclododecanone in 274 g of isopropylcyclohexane were introduced at 40° C. 5.0 g of catalyst (TS1, Degussa AG), 73 g of water, 2.55 g of alkane sulfonate (Marlon PS 30 from Sasol GmbH) and 8.28 g of citric acid were added as cocatalyst building block. The reactor was heated to 95° C. and depressurized to 0.1 bar (superatmospheric pressure), then ammonia gas was slowly forced in up to a pressure of 1.6 bar. Approximately 20 g of ammonia were added.

During the reaction, the pressure was kept constant via a gentle off-gas stream, and optionally ammonia gas was replenished. Over a period of 180 minutes, 37.0 ml of a 50% strength by weight hydrogen peroxide solution (equivalent to 650 mmol of $H_2O_2$) were added via a pump. After completion of peroxide addition, the reaction mixture was allowed to react for a further 60 minutes.

The conversion rate was followed by gas chromatography (GC) during the reaction and hydrogen peroxide was determined iodometrically. After 240 minutes the conversion rate was 97.2%, equivalent to a peroxide selectivity of 74.7%.

Example 2

The experiment was repeated in accordance with Example 1. The addition time was 300 minutes and the post-reaction time 60 minutes. After 360 minutes the conversion rate was 99.4%. 1.44 equivalents of $H_2O_2$ were consumed, equivalent to a peroxide selectivity of 69.1%.

Example 3 (Comparative Example)

The experiment was repeated in accordance with example 2. 54.7 g (300 mmol) of cyclododecanone in 310 g of isopropylcyclohexane were introduced at 40° C. 2.5 g of catalyst (TS1, Degussa AG), 73 g of water and 2.55 g of alkane sulfonate (Marlon PS 30 from Sasol GmbH) were added. After 360 minutes, the conversion rate was 20.0%, 2.40 equivalents of $H_2O_2$ were consumed, equivalent to a peroxide selectivity of 8.4%. It was found that without cocatalyst only very poor conversion rates and selectivities were achieved.

Example 4 (Comparative Example)

50 mmol of cyclododecanone in 50 ml of isopropylcyclohexane were introduced at 60° C. into a nitrogen-purged, heatable 100 ml glass jacketed reactor equipped with gas inlet agitator (1500 rpm), purge and pressure regulator. 1.0 g of catalyst (TS1, Degussa AG) were added. The reactor was heated to 60° C., and then ammonia gas was slowly forced in up to a pressure of 1.1 bar.

During the reaction the pressure was kept constant via a gentle off gas stream, optionally ammonia gas was replenished. Over a period of 180 minutes, 100 mmol of a 50% strength by weight hydrogen peroxide solution were added via a pump. When peroxide addition was complete, the reaction mixture was allowed to react further for 120 minutes. The conversion rate was followed by GC during the reaction and hydrogen peroxide was determined iodometrically. After 300 minutes the conversion rate was 2.9%; this corresponds to a peroxide selectivity of 1.4%. It was found that without cocatalyst and without interphase contactor, only very poor conversion rates and selectivities were achieved.

Examples 5–10

The experiment was repeated in accordance with Example 3, except that the metering time of $H_2O_2$ is 240 minutes and the post-reaction time is 60 minutes and various ammonium salts were added. All salts were added at the same concentration of 0.1 mol/l based on the total two-phase mixture The results are summarized in Table 1.

TABLE 1

| Example No. | Ammonium salt | Conversion rate [%] | $H_2O_2$ selectivity |
|---|---|---|---|
| 3 | none | 20 | 8 |
| 5 | acetate | 77 | 39 |
| 6 | citrate | 90 | 45 |
| 7 | glutarate | 66 | 33 |
| 8 | benzoate | 89 | 44 |
| 9 | phosphate | 40 | 20 |
| 10 | sulfate | 68 | 34 |

German patent application 10158352.4 filed Nov. 28, 2001, is incorporated herein by reference.

Numerous modifications and variations on the present invention are possible in light of the above teachings. It is therefore to be understood that within the scope of the appended claims, the invention may be practiced otherwise than as specifically described herein.

What is claimed is:

1. A process for preparing an oxime, comprising:
   reacting a ketone or an aldehyde with hydrogen peroxide and ammonia in a system of one aqueous phase and one phase consisting of a hydrocarbon inert under the reaction conditions, in the presence of a catalyst system which comprises at least two components; and
   wherein a first component of the catalyst system is present in heterogeneous form and is based on titanium, silicon and oxygen; and
   wherein a second component is a homogeneously dissolved or suspended ammonium salt; and
   wherein at least one interphase contactor is present.

2. The process as claimed in claim 1, wherein the interphase contactor is a surfactant, a mixture of surfactants or a mixture of a surfactant and a phase-transfer catalyst.

3. The process as claimed in claim 1, wherein the interphase contactor comprises an alkane sulfonate.

4. The process as claimed in claim 1, wherein the first component of the catalyst is a titanium silicalite.

5. The process as claimed in claim 1, wherein the first component of the catalyst is the titanium silicalite TSI.

6. The process as claimed in claim 1, wherein, in addition to the component based on titanium, silicon and oxygen, at least one further component comprising an acidic solid which contains an inorganic or organic support material is present;

wherein either the support material itself has Lewis acid or Brönsted acid properties; or wherein a Lewis acid functional group or Brönsted acid functional group or Brönsted acid functional group is applied physically or chemically to the support material.

7. The process as claimed in claim 6, wherein the support material is an acidic inorganic solid based on aluminum oxide or aluminosilicate.

8. The process as claimed in claim 6, wherein the support material is an organic solid based on an acidic ion exchanger or a strongly acidic ion exchanger.

9. The process as claimed in claim 6, wherein a weight ratio of catalyst to support material is from 0.1:1 to 10:1.

10. The process as claimed in claim 6, wherein a) said catalyst or b) said catalyst and said support material are in powder form.

11. The process as claimed in claim 6, wherein said catalyst and said support material are in the form of shaped bodies.

12. The process as claimed in claim 11, wherein the support material simultaneously acts as a binder of the shaped body.

13. The process as claimed in claim 1, wherein the heterogeneous catalyst is present in the form of a fixed bed.

14. The process as claimed in claim 1, wherein the anion of the ammonium salt is a halide ion, a sulfate ion, a hydogensulfate ion, a nitrate ion, a phosphate ion or an anion of a carboxylic acid.

15. The process as claimed in claim 13, wherein said ammonium salt is ammonium formate, ammonium acetate, ammonium propionate, ammonium oxalate, aminonium glutarate, ammonium malonate, ammonium citrate or ammonium benzoate.

16. The process as claimed in claim 1, wherein a reaction temperature is between 20° C. and 150° C.

17. The process as claimed in claim 1, wherein a reaction temperature is between 60° C. and 100° C.

18. The process as claimed in claim 1, wherein a pressure is from 1 bar to 10 bar.

19. The process as claimed in claim 1, wherein acetophenone or a cyclic ketone having from 8 to 20 carbon atoms is ammoximated.

20. The process as claimed in claim 18, wherein cyclododecanone is ammoximated.

* * * * *